(12) United States Patent
Moss

(10) Patent No.: US 6,758,827 B2
(45) Date of Patent: Jul. 6, 2004

(54) ANGULARLY ADJUSTABLE TRACTION APPARATUS

(76) Inventor: John S. Moss, 1400 Washington Ave., Fredericksburg, VA (US) 22401

( * ) Notice: Subject to any disclaimer, the term of this patent is extended or adjusted under 35 U.S.C. 154(b) by 196 days.

(21) Appl. No.: 09/944,445

(22) Filed: Aug. 31, 2001

(65) Prior Publication Data

US 2002/0042586 A1 Apr. 11, 2002

Related U.S. Application Data

(63) Continuation-in-part of application No. 09/679,770, filed on Oct. 5, 2000, now Pat. No. 6,533,743.

(51) Int. Cl.[7] .................................................. A61F 5/00
(52) U.S. Cl. ........................................................ 602/33
(58) Field of Search ............. 602/32–40; 606/240–244; 128/845, 878, 879

(56) References Cited

U.S. PATENT DOCUMENTS

| | | | | |
|---|---|---|---|---|
| 2,306,031 A | * | 12/1942 | Anderson et al. ............... | 5/602 |
| 2,590,739 A | * | 3/1952 | Wagner et al. ................. | 602/39 |
| 2,909,175 A | * | 10/1959 | Kinnear ......................... | 602/33 |
| 3,087,489 A | * | 4/1963 | Gilbert et al. ................. | 602/33 |
| 3,139,884 A | * | 7/1964 | Stryker .......................... | 602/39 |
| 3,390,675 A | * | 7/1968 | Giannestras .................. | 602/33 |
| 3,745,996 A | * | 7/1973 | Rush ............................. | 602/39 |
| 3,850,166 A | | 11/1974 | Tamny et al. .................. | 128/84 |
| 3,875,356 A | * | 4/1975 | Heim et al. ................ | 200/52 R |
| 4,445,506 A | * | 5/1984 | Johansson et al. ............ | 602/39 |
| 4,526,355 A | * | 7/1985 | Moore et al. .................. | 5/624 |
| 4,616,637 A | * | 10/1986 | Caspari et al. ................ | 602/39 |
| 4,782,827 A | * | 11/1988 | Paratte ......................... | 602/35 |
| 4,886,258 A | * | 12/1989 | Scott ............................. | 5/624 |
| 5,020,525 A | * | 6/1991 | Ewing et al. ................. | 602/27 |
| 5,025,802 A | * | 6/1991 | Laico et al. ................ | 128/882 |
| 5,063,918 A | * | 11/1991 | Guhl ............................ | 602/40 |
| 5,074,291 A | | 12/1991 | Carter ......................... | 128/84 |
| 5,290,220 A | * | 3/1994 | Guhl ............................ | 602/33 |
| 5,441,480 A | | 8/1995 | Kane et al. ................... | 602/36 |
| 5,632,726 A | * | 5/1997 | Repice et al. ................. | 602/36 |
| 5,722,941 A | * | 3/1998 | Hart ............................. | 602/32 |
| 5,775,334 A | * | 7/1998 | Lamb et al. ................ | 128/845 |
| 5,865,780 A | | 2/1999 | Tuite | |
| 5,881,730 A | * | 3/1999 | Burger ....................... | 128/878 |
| 5,961,512 A | * | 10/1999 | Purnell ......................... | 606/1 |
| 6,467,487 B1 | * | 10/2002 | Rios ........................... | 128/869 |
| 6,533,743 B1 | * | 3/2003 | Moss ........................... | 602/32 |
| 6,533,744 B1 | * | 3/2003 | Stanish et al. ............... | 602/33 |

* cited by examiner

Primary Examiner—Nicholas D. Lucchesi
Assistant Examiner—Huong Q. Pham
(74) Attorney, Agent, or Firm—Sturm & Fix LLP

(57) ABSTRACT

An improved angularly adjustable traction apparatus (10) including a generally rectangular platform member (20) having an elongated track groove (30) disposed in one side (23) for slidably receiving a limb immobilizing unit (12) and a pulley unit (13) having a traction device (90). Both the limb immobilizing unit (12) and the pulley unit (13) are provided with securing elements (50), (50') etc. for captively engaging the limb immobilizing (12) and pulley (13) units at selected locations within the track groove (30) and a pair of anchor units (15) associated with portions of the limb immobilizing (12) and pulley (13) units to maintain their angular orientation relative to the platform member (20).

18 Claims, 3 Drawing Sheets

ANGULARLY ADJUSTABLE TRACTION APPARATUS

CROSS REFERENCE TO RELATED APPLICATIONS

This is a continuation-in-part application of my co-pending patent application Ser. No. 09/679,770 filed on Oct. 5, 2000 now U.S. Pat. No. 6,533,743 and entitled "Angularly Adjustable Traction Apparatus", the content of which is incorporated herein by reference.

BACKGROUND OF THE INVENTION

1. Field of the Invention

The present invention relates to the field of traction apparatus in general, and in particular to a traction apparatus having angularly and laterally adjustable structural components to accommodate individual patients and/or medical procedures.

2. Description of Related Art

As can be seen by reference to the following U.S. Pat. Nos. 5,074,291; 3,850,166; 5,441,480; 5,961,512; and 5,632,726, the prior art is replete with myriad and diverse arrangements for immobilizing and/or placing a patient's limbs in a traction mode.

While all of the aforementioned prior art constructions are more than adequate for the basic purpose and function for which they have been specifically designed, they are uniformly deficient with respect to their failure to provide a simple, efficient, and practical apparatus for applying traction to a patient's limbs while the patient reclines in a supine position and wherein the apparatus employs both laterally and angularly adjustable components to accommodate the needs of individual patients.

As most physicians are well aware, the proper application of traction forces is a necessary requirement when setting bone fractures and performing other related medical procedures.

As a consequence of the foregoing situation, there has existed a longstanding need in the medical field for a new and improved angularly adjustable traction apparatus that can be employed in both the straight anterior and direct superior modes, as well as positions intermediate thereof, and the provision of such a device is a stated objective of the present invention.

BRIEF SUMMARY OF THE INVENTION

Briefly stated, the angularly adjustable traction apparatus that forms the basis of the invention comprises in general, a main support unit, a limb immobilizing unit, a pulley unit, a track unit, and a pair of anchor units wherein the limb immobilizing and pulley units are angularly and laterally adjustable relative to the main support unit and the track unit and the pulley unit is vertically adjustable as well.

As will be explained in greater detail further on in the specification, the main support unit comprises a base platform member that is dimensioned to fit under a patient's upper torso and the track unit comprises an elongated track groove formed in the platform member and dimensioned to slidably receive the limb immobilizing, pulley, and pair of anchor units.

While the subject matter of this invention produces the same functional results as that produced in my co-pending application, the specific arrangement of structural components improves a surgeon's access to the patient's immobilized limbs while maximizing the x-ray field of view of the patient's limb.

Furthermore, the apparatus of this invention employs a plurality of quick release securing elements for angularly adjusting and maintaining the desired angular orientation of the various structural components. The pair of anchor units are specifically designed to prevent the displacement of the limb immobilizing and pulley units once their desired positioning and angular orientations have been achieved.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein.

DETAILED DESCRIPTION OF THE INVENTION

Figure 1:
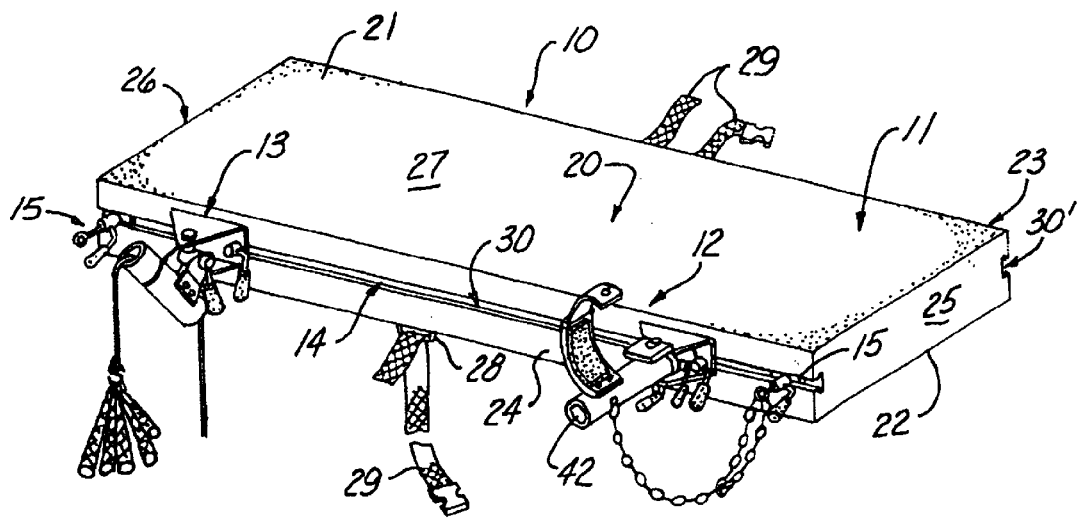
FIG. 1 is a perspective view of the improved adjustable angle traction apparatus that forms the basis of this invention in use.

As can be seen by reference to the drawings, and in particular to FIG. 1, the angularly adjustable traction apparatus that forms the basis of the present invention is designated generally by the reference number 10. The apparatus 10 comprises in general, a main support unit 11, a limb immobilizing unit 12, a pulley unit 13, a track unit 14, and a pair of anchor units 15. These units will now be described in seriatim fashion.

As shown in FIG. 1, the preferred embodiment, the main support unit 11 comprises in general an elongated flat rectangular base platform member 20 dimensioned to underlie a substantial portion of a patient's torso and rest upon the top of a medical examination table or the like. The platform member 20 has top 21, a bottom 22, a pair of elongated sides 23, 24 a front side 25, and a rear side 26. The top 21 may be provided with a padded or cushioned surface 27 and the bottom 22 may be provided with one or more buckles 28 that are adapted to receive restraining straps 29.

Figure 2:
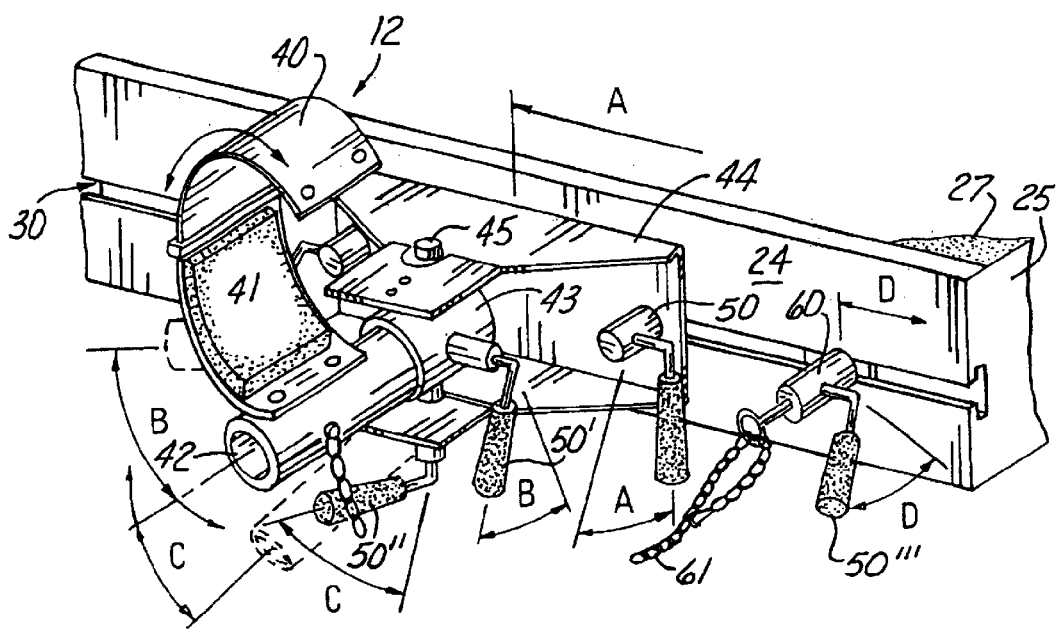
FIG. 2 is an isolated detail view of the limb immobilizing unit and one of the anchor units.

As shown in FIGS. 1 and 2, the track unit 14 comprises an elongated recessed track groove 30 extending along at least one of the elongated sides 23, 24 of the platform member 20. The track groove 30 intersects at least one of the front 25 and rear 26 sides of the platform member 20 for reasons that will become apparent presently.

As can best be seen by reference to FIG. 2, the limb immobilizing unit 12 comprises a generally C-shaped limb engaging member 40 having a padded interior 41 and being secured in a tangential fashion on a hollow tubular support arm 42 releasably received in a swiveling angularly adjustable collar element 43 suspended within a first support bracket 44 that is slidably received within the track groove 30 in the platform member 20.

In addition, the support bracket 44 is further provided with one or more securing elements 50 that will captively engage the support bracket 44 at a desired location along the track groove 30 in the platform member 20 and the collar element 43 is also provided with a securing element 50' that will releasably engage the hollow tubular support arm 42 so that the orientation of the limb engaging member 40 can be reversed 180° when desired.

As can also be appreciated by reference to FIG. 1, the collar element 43 is pivotally mounted within the support bracket 44 as at 45 to vary the angular orientation of the support arm 42 relative to the support bracket 44 in the horizontal plane. The collar element 43 is also provided with a securing element 50" to captively engage the collar element 43 at a desired angular orientation relative to the support bracket 44.

Furthermore, one of the anchor units 15 is operatively associated with the limb immobilizing unit 12 and comprises an anchor bracket 60 slidably received in the track groove 30 in the platform member 20. The anchor bracket is operatively associated with an adjustable length tether element 61 such as a chain that is fixedly secured on one end to the support arm 42 of the limb engaging member 40 to prevent the support arm 42 from moving from its selected orientation when the traction forces are applied to a patient's limb. The anchor bracket 60 is also provided with a securing element 50''' to maintain the anchor bracket 60 at a desired location within the track groove 30.

Figure 3:
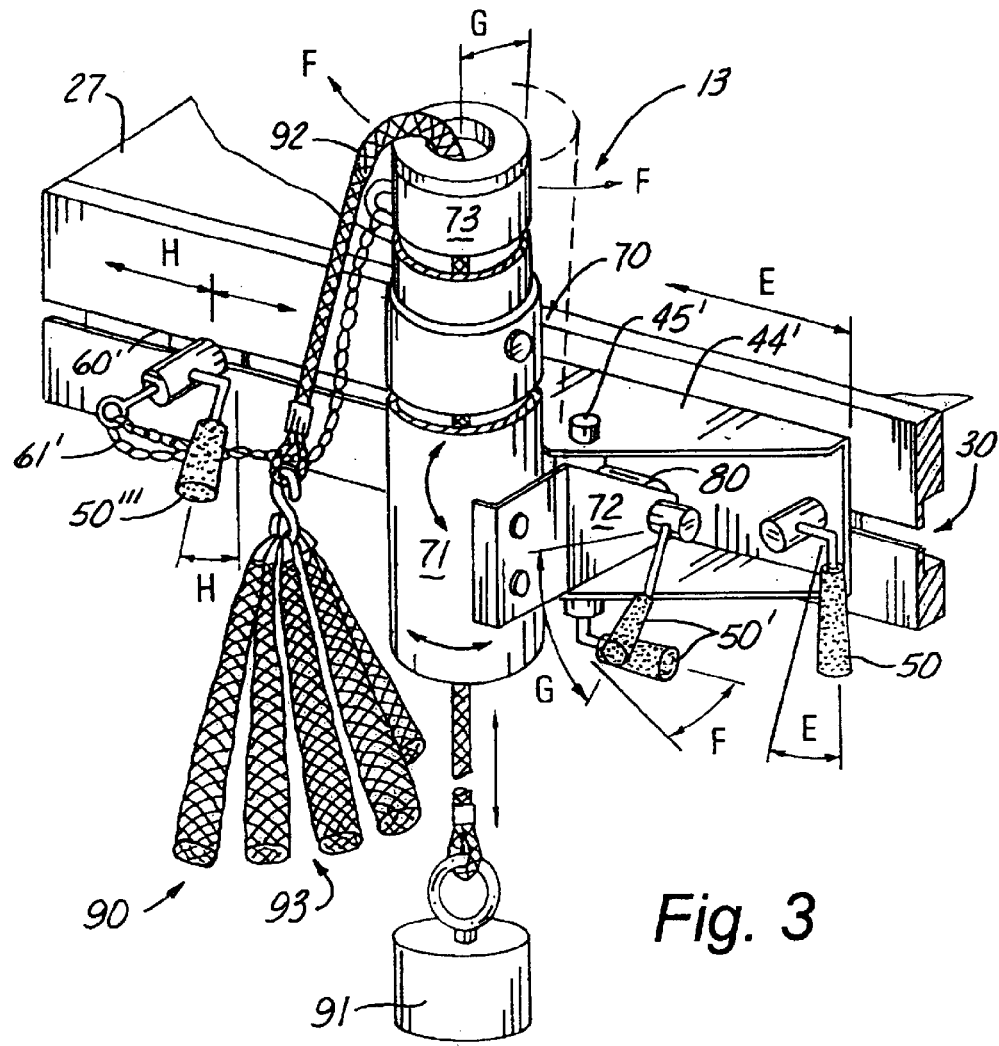
FIG. 3 is an isolated detail view of the pulley unit and the other of the anchor units.

Turning now to FIG. 3, it can be seen that the pulley unit 13 comprises an extensible pulley tower 70 mounted for pivotal movement in both the vertical and horizontal planes in a second support bracket 44' that is slidably received within the track groove 30 in the platform member 20 and also provided with securing elements 50 to captively engage the second support bracket 44' at a desired location within the track groove 30 as previously described.

Figure 5:
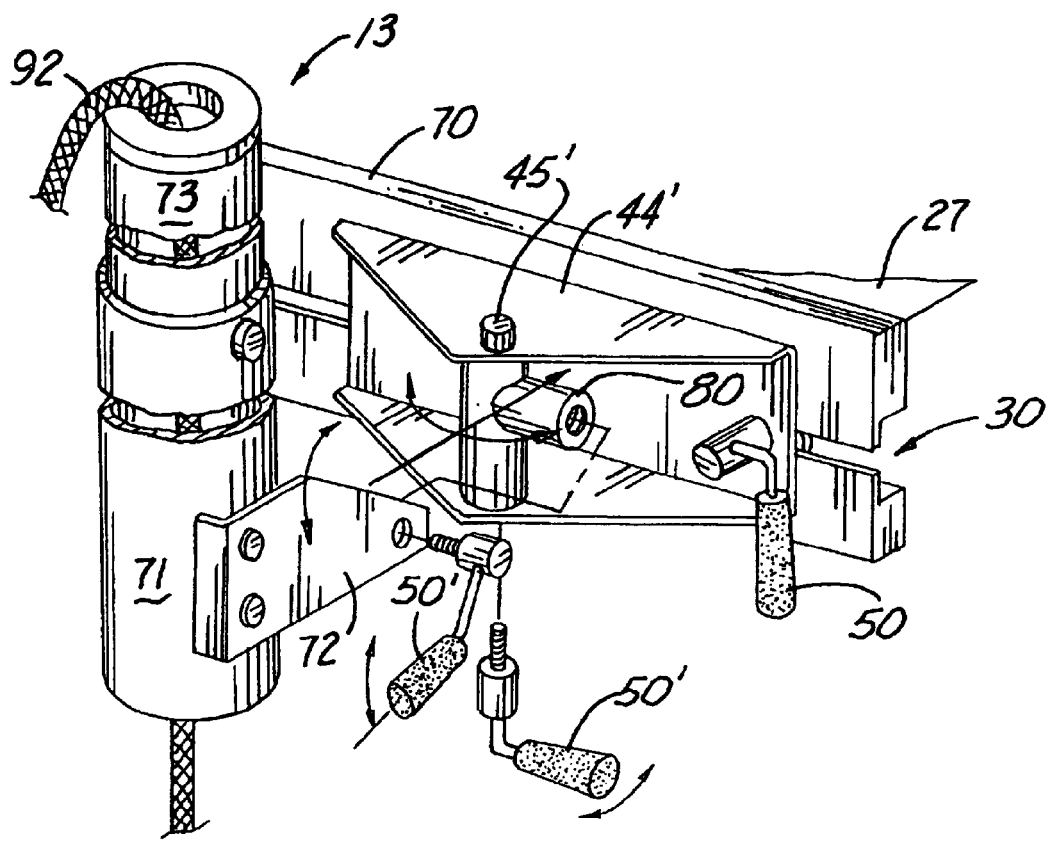

As shown in FIGS. 3 and 5, the pulley tower 70 has a lower cylindrical portion 71 provided with a pair of flange ears 72 whose inboard ends are rotatably suspended relative to the cross arms of a cruciform shaped pivot element 80 whose stem is vertically pivotally suspended within the second support bracket 44' as at 45'.

Still referring to FIGS. 3 and 5, it can be seen that the pulley tower also includes a hollow upper cylindrical portion 73 that is telescopically received in the lower cylindrical portion 71 to vary the effective length of the pulley tower 70 in a well recognized fashion. Both the upper 71 and lower 73 portions of the pulley tower are dimensioned to receive a traction applying member designated generally as 90 which includes a traction weight 91 connected on one end of a flexible traction cable 92 whose other end is releasably associated with a limb engaging element 93 such as the finger cot arrangement depicted in FIGS. 3 and 5.

As can also be seen by reference to FIGS. 3 and 5, the upper portion 73 of the pulley tower is also attached to one end of a tether element 61' whose other end is associated with the other anchor bracket 60' for reasons that previously have been discussed herein.

As can also be seen by reference to FIG. 3, the upper portion 73 of the pulley tower is also attached to one end of a tether element 61' whose other end is associated with the other anchor bracket 60' for reasons that previously have been discussed herein.

Figure 4:
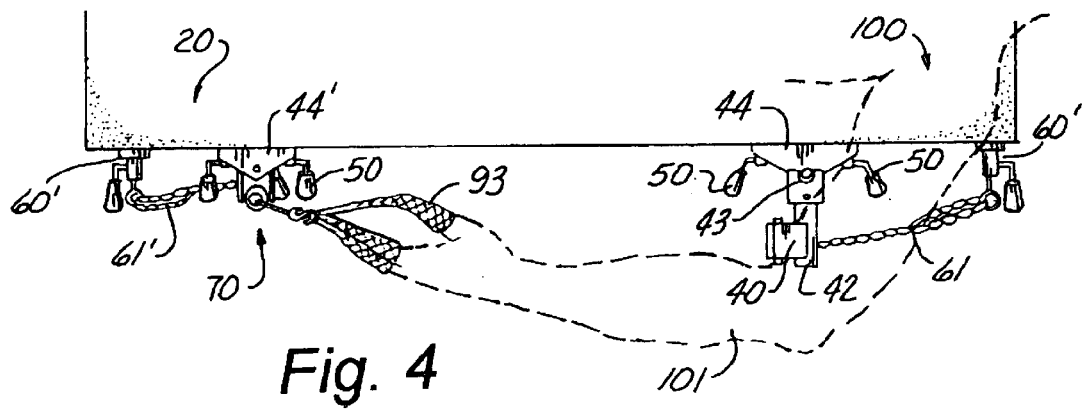
FIG. 4 is a top plan view demonstrating the relative position of the limb immobilizing unit, the pulley unit and both of the anchor units relative to both the main support unit and a patient's limb being placed into traction and, FIG. 5 is an exploded perspective view of the pivoting arrangement of the limb immobilizing unit.

Turning now to FIG. 4, it can be seen that the apparatus 10 is employed to immobilize a patient's limb 101 while traction forces are applied thereto. To accomplish this result, a patient is placed in a supine position upon the top of the platform member 20 and the limb engaging member 40 is angularly adjusted in both the horizontal and vertical planes to engage the patient's limb; whereupon, the first anchor bracket 60 is laterally adjusted in the track groove 30 to prevent the limb immobilizing unit 12 from becoming displaced.

At this juncture, the pulley tower 70 is vertically and horizontally angularly adjusted relative to the second support bracket 44' after the second support bracket 44' has been selectively positioned and secured within the track groove 30 and the other anchor bracket 60' causes the tether element 61' to resist the displacement of the upper portion 73 of the pulley tower.

The limb engaging element 93 is then attached to the free end of the patient's limb 101 and the weight 91 will place the limb 101 into traction in a well recognized manner.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

I claim:

1. An improved angularly adjustable traction apparatus for placing a patient's selected limb into traction wherein the apparatus comprises:

a main support unit including a generally elongated rectangular platform member having a top, a bottom, opposed elongated sides, a front side, and a rear side;

a track unit including at least one elongated track groove formed in one of the elongated opposed sides of the platform member wherein the at least one track groove further extends through at least one of the front and rear sides of the platform member;

a traction device including a weight, a traction cable, and a limb engaging element;

a limb immobilizing unit including a first support bracket slidably received in said at least one track groove a collar element and a support arm having a generally C-shaped limb engaging member;

wherein, the collar element is pivotally connected to the first support bracket and further dimensioned to receive said support arm and, a pulley unit including a second support bracket slidably received in said at least one track groove wherein the second support bracket is provided with a pivoting pulley tower dimensioned to accommodate a portion of the traction device.

2. The apparatus as in claim 1 wherein the collar element is pivotally associated with the first support bracket about a vertical axis.

3. The apparatus as in claim 2 wherein the pulley tower is pivotally associated with the second support bracket about a vertical axis.

4. The apparatus as in claim 2 wherein the pulley tower is pivotally associated with the second support bracket about a horizontal axis.

5. The apparatus as in claim 2 wherein the pulley tower is pivotally associated with the second support bracket about a vertical and a horizontal axis.

6. The apparatus as in claim 1 wherein the support arm is rotatably associated with the collar element about a horizontal axis.

7. The apparatus as in claim 2 wherein the support arm is rotatably associated with the collar element about a horizontal axis.

8. The apparatus as in claim 3 wherein the support arm is rotatably associated with the collar element about a horizontal axis.

9. The apparatus as in claim 4 wherein the support arm is rotatably associated with the collar element about a horizontal axis.

10. The apparatus as in claim 5 wherein the support arm is rotatably associated with the collar element about a horizontal axis.

11. The apparatus as in claim 10 further comprising:

a plurality of securing elements for captively engaging the support arm and the collar element at a desired angular orientation relative to one another.

12. The apparatus as in claim 1 wherein the pulley tower has a hollow lower portion dimensioned to telescopically receive a hollow upper portion.

13. The apparatus as in claim 11 wherein the pulley tower has a hollow lower portion dimensioned to telescopically receive a hollow upper portion.

14. The apparatus as in claim 1 further comprising:

a pair of anchor units wherein each anchor unit is associated with one of the limb immobilizing and pulley units and comprises an anchor bracket slidably disposed in the at least one track groove and attached on one end of a tether element wherein the other end of the tether element is operatively associated with a selected portion of one of the limb immobilizing and pulley units.

15. The apparatus as in claim 12 further comprising:

a pair of anchor units wherein each anchor unit is associated with one of the limb immobilizing and pulley units and comprises an anchor bracket slidably disposed in the at least one track groove and attached on one end of a tether element wherein the other end of the tether element is operatively associated with a selected portion of one of the limb immobilizing and pulley units.

16. The apparatus as in claim 15 wherein one of the tether elements is attached to the upper portion of the pulley tower and the other tether element is attached to said support arm.

17. The apparatus as in claim 1 further comprising:

means for captively engaging the limb immobilizing unit and the pulley unit at a desired location within the track groove.

18. The apparatus as in claim 16 further comprising:

means for captively engaging the anchor units, the limb immobilizing unit, and the pulley unit at desired locations within the track groove.

* * * * *